United States Patent [19]

Kawamatsu et al.

[11] 4,444,779

[45] * Apr. 24, 1984

[54] THIAZOLIDINE DERIVATIVES

[75] Inventors: Yutaka Kawamatsu, Kyoto; Takeshi Fujita, Takarazuka, both of Japan

[73] Assignee: Takeda Chemical Industries, Ltd., Osaka, Japan

[*] Notice: The portion of the term of this patent subsequent to Jul. 20, 1999 has been disclaimed.

[21] Appl. No.: 476,017

[22] Filed: Mar. 15, 1983

Related U.S. Application Data

[62] Division of Ser. No. 396,093, Jul. 7, 1982, which is a division of Ser. No. 258,554, Apr. 29, 1981, Pat. No. 4,340,605, which is a division of Ser. No. 62,512, Jul. 27, 1979, Pat. No. 4,287,200.

[30] Foreign Application Priority Data

Aug. 4, 1978 [JP] Japan .................. 53-95673

[51] Int. Cl.³ .................. C07D 277/20; A61K 31/425
[52] U.S. Cl. .................. 424/263; 424/270; 546/284; 548/201; 548/202; 548/203
[58] Field of Search .............. 548/200, 201, 203; 424/263, 270; 546/280, 284

[56] References Cited

U.S. PATENT DOCUMENTS 4,340,605  7/1982  Kawamatsu et al. ............. 424/263

Primary Examiner—Nicholas S. Rizzo
Attorney, Agent, or Firm—Wenderoth, Lind & Ponack

[57] ABSTRACT

Thiazolidine derivatives of the general formula:

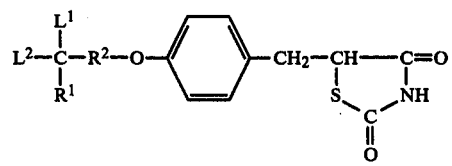

[wherein $R^1$ is alkyl, cycloalkyl, phenylalkyl, phenyl, a five- or six-membered heterocyclic group including one or two hetero-atoms selected from the group consisting of nitrogen, oxygen and sulfur or a group of the formula

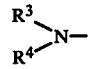

(where $R^3$ and $R^4$ are the same or different and each is lower alkyl or $R^3$ and $R^4$ are combined to each other either directly or as interrupted by a hetero-atom selected from the group consisting of nitrogen, oxygen and sulfur to form a five- or six-membered ring); $R^2$ means a bond or a lower alkylene group; $L^1$ and $L^2$ are the same or different and each is lower alkyl or $L^1$ and $L^2$ are combined to form an alkylene group, provided that when $R^1$ is other than alkyl, $L^1$ and $L^2$ may further be hydrogen, respectively] are novel compounds and useful as, for example, remedies for diabetes, hyperlipemia and so on of mammals including human beings.

6 Claims, No Drawings

THIAZOLIDINE DERIVATIVES

This is a division of application Ser. No. 396,093 filed July 7, 1982, which is a division of application Ser. No. 258,554, filed Apr. 29, 1981, now U.S. Pat. No. 4,340,605, which in turn is a division of application Ser. No. 62,512 filed July 27, 1979, now U.S. Pat. No. 4,287,200.

This invention relates to novel thiazolidine derivatives having hypolipidemic and hypoglycemic activities with low toxicity. More particularly, this invention relates to thiazolidine derivatives of the general formula:

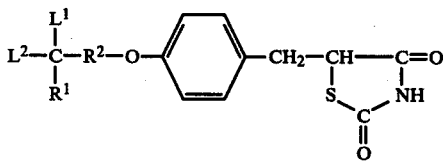

[wherein $R^1$ is alkyl, cycloalkyl, phenylalkyl, phenyl, a five- or six-membered heterocyclic group including one or two hetero-atoms selected from the group consisting of nitrogen, oxygen and sulfur, or a group of the formula

(where $R^3$ and $R^4$ are the same or different and each means lower alkyl or $R^3$ and $R^4$ are combined to each other either directly or as interrupted by a hetero-atom selected from the group consisting of nitrogen, oxygen and sulfur to form a five- or six-membered ring as taken together with the nitrogen atom adjacent to $R^3$ and $R^4$); $R^2$ is a bond or a lower alkylene group; $L^1$ and $L^2$ may be the same or different and each is lower alkyl or $L^1$ and $L^2$ are combined to each other to form an alkylene group, provided that when $R^1$ is other than alkyl, $L^1$ and $L^2$ may further be hydrogen, respectively].

Referring to the general formula (I), the alkyl group $R^1$ may be a straight-chain or branched alkyl of 1 to 10 carbon atoms, such as methyl, ethyl, n-propyl, i-propyl, n-butyl, i-butyl, t-butyl, n-pentyl, i-pentyl, n-hexyl, n-heptyl, n-octyl, n-nonyl and n-decyl; the cycloalkyl group $R^1$ may be a cycloalkyl group of 3 to 7 carbon atoms, such as cyclopropyl, cyclopentyl, cyclohexyl, and cycloheptyl; and the phenylalkyl group $R^1$ may be a phenylalkyl group of 7 to 11 carbon atoms such as benzyl and phenethyl. As examples of the heterocyclic group $R^1$ may be mentioned 5- or 6-membered groups each including 1 or 2 hetero-atoms selected from among nitrogen, oxygen and sulfur, such as pyridyl, thienyl, furyl, thiazolyl, etc. When $R^1$ is

the lower alkyls $R^3$ and $R^4$ may each be a lower alkyl of 1 to 4 carbon atoms, such as methyl, ethyl, n-propyl, i-propyl and n-butyl. When $R^3$ and $R^4$ are combined to each other to form a 5- or 6-membered heterocyclic group as taken together with the adjacent N atom, i.e. in the form of

this heterocyclic group may further include a hetero-atom selected from among nitrogen, oxygen and sulfur, as exemplified by piperidino, morpholino, pyrrolidino and piperazino. The lower alkylene group $R^2$ may contain 1 to 3 carbon atoms and, thus, may for example be methylene, ethylene or trimethylene. The bond $R^2$ is equivalent to the symbol "-", "." or the like which is used in chemical structural formulas, and when $R^2$ represents such a bond, the compound of general formula (I) is represented by the following general formula (II):

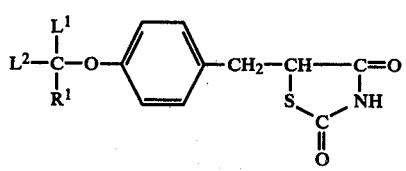

Thus, when $R^2$ is a bond, the atoms adjacent thereto on both sides are directly combined together. As examples of the lower alkyls $L^1$ and $L^2$, there may be mentioned lower alkyl groups of 1 to 3 carbon atoms, such as methyl and ethyl. The alkylene group formed as $L^1$ and $L^2$ are joined together is a group of the formula—$(CH_2)_n$—[where n is an integer of 2 to 6.] The cycloalkyl, phenylalkyl, phenyl and heterocyclic groups mentioned above, as well as said heterocyclic group

may have 1 to 3 substituents in optional positions on the respective rings. As examples of such substituents may be mentioned lower alkyls (e.g. methyl, ethyl, etc.), lower alkoxy groups (e.g. methoxy, ethoxy, etc.), halogens (e.g. chlorine, bromine, etc.) and hydroxyl. The case also falls within the scope of the general formula [I] that an alkylenedioxy group of the formula —O—$(CH_2)_m$—O— [m is an integer of 1 to 3], such as methylenedioxy, is attached to the two adjacent carbon atoms on the ring to form an additional ring.

The compound (I) according to this invention can be converted to various salts by procedures known per se. For example, when the heterocyclic group $R^1$ includes a tertiary nitrogen atom, or $R^1$ means a group of the formula

the compound (I) can be converted to acid salts with acids, such as hydrochloric acid, sulfuric acid, acetic acid, oxalic acid, etc. When $R^1$ does not include a tertiary nitrogen atom, the compound may be converted to salts with cations such as a sodium ion, a potassium ion, a calcium ion, or an ammonium ion, etc.

The thiazolidine derivative (I) according to this invention has activity to lower the blood sugar and triglyceride levels in mice (KKAy) with spontaneous diabetes and is expected to be of value in the treatment of hyperlipemia, diabetes and their complications in mammals including human beings. The compound (I) has low toxicity. For example, the $LD_{50}$ value of 5-[4-(1-methylcyclohexylmethyloxy)benzyl]thiazolidine-2,4-dione in a rat is more than 10 g/kg. (P.O.). The compound (I) may be orally administered in such dosage forms as tablets, capsules, powders, granules, etc. or by other routes in such forms as injections, suppositories, pellets and so on. Taking the treatment of hyperlipemia as an example, the compound may be orally or otherwise administered at a normal daily dose level of 50 mg to 1 gram per adult human. For the treatment of diabetes, the compound (I) may be orally or otherwise administered at a normal daily dose of 10 mg to 1 gram per adult human.

The thiazolidine derivative (I) of this invention may be produced, for example, by the following methods.

(1) The thiazolidine derivative (I) can be produced by the steps of reacting a compound of general formula (III) with thiourea to obtain an 2-iminothiazolidine derivative of general the formula (IV) and, then, hydrolyzing the last-mentioned derivative (IV).

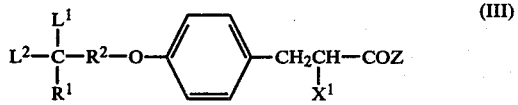

(III)

[wherein $R^1$, $R^2$, $L^1$ and $L^2$ have the meanings respectively defined hereinbefore; $X^1$ means halogen (e.g. chlorine, bromine, etc.), alkylsulfonyloxy (e.g. methylsulfonyloxy, etc.) or arylsulfonyloxy (e.g. toluenesulfonyloxy, etc.); Z is lower alkoxy (e.g. methoxy, ethoxy, etc.), hydroxyl, amino or a group of the formula —OM (M is, for example, an alkali metal atom, e.g. Na, K, etc., or $NH_4$)]

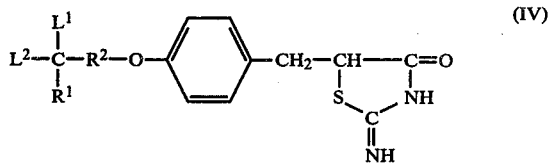

(IV)

[wherein $R^1$, $R^2$, $L^1$ and $L^2$ have the meanings respectively defined hereinbefore]

The compound (IV) may tautomerically take the form as below:

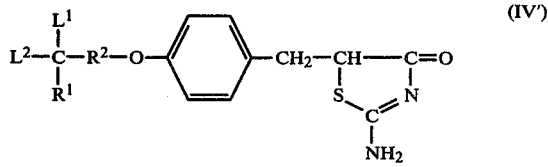

(IV')

[wherein $R^1$, $R^2$, $L^1$ and $L^2$ have the meanings respectively defined hereinbefore] The compound (IV') is also included within the scope of this invention. In this specification, the nomenclature and formula of these compounds are described en bloc as "2-iminothiazolidine derivative" and as formula (IV), respectively.

The reaction between a compound (III) and thiourea is normally conducted in a solvent. As examples of such solvent may be mentioned alcohols (e.g. methanol, ethanol, propanol, butanol, ethylene glycol monomethyl ether, etc.), ethers (e.g. tetrahydrofuran, dioxane, etc.), acetone, dimethylsulfoxide, sulfolane, dimethylformamide, etc. While the relative amounts of starting materials need not be critically controlled, it is normally desirable to employ a slight excess of thiourea based on compound (III). Thus, 1 to 2 molecular equivalents of thiourea is preferably employed relative to compound (III). While the conditions of reaction such as reaction temperature and time depend on such factors as the starting material, solvent, etc., this reaction is normally carried out at the boiling point of the solvent used or at 100° to 130° C. for a few to ten and odd hours. The sparingly soluble imino-compound (IV) is produced in the above manner. This imino-compound (IV) may be isolated prior to the following hydrolysis step or the reaction mixture containing (IV) may be directly hydrolyzed. In the hydrolysis step, the imino-compound (IV) is heated in a suitable solvent (e.g. sulfolane) and in the presence of water and mineral acid. The acid just mentioned is added normally in a proportion of 0.1 to 10 molecular equivalents, preferably 0.2 to 3 equivalents, based on compound (III), while water is used normally in large excess based on compound (III). The heating time normally ranges from a few hours to 10 and odd hours.

(2) The thiazolidine derivative (I) can further be produced by subjecting a compound of formula:

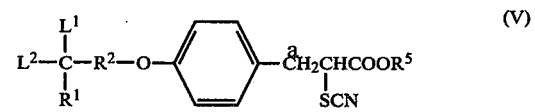

(V)

[wherein $L^1$, $L^2$, $R^1$ and $R^2$ have the meanings given above, and $R^5$ means alkyl having 1 to 4 carbon atoms (e.g. methyl, ethyl, n-propyl, n-butyl, t-butyl, etc.), aryl having 6 to 8 carbon atoms (e.g. tolyl, etc.) or aralkyl having 7 to 8 carbon atoms (e.g. benzyl, etc.)] to a cyclization reaction. This cyclization reaction is usually carried out by hydrolizing a compound (V) with water. The hydrolysis is generally conducted in the presence of a catalyst, examples of which include hydrogen halides (e.g. hydrogen chloride, hydrogen bromide), mineral acids such as hydrochloric acid, sulfuric acid, etc. The catalyst may generally be used in an amount of 20 to 50 mol equivalents relative to the compound (V). This reaction may be conducted in the presence of an organic solvent such as alcohol (e.g. methanol, ethanol, etc.). While the reaction temperature varies with the type of catalyst used, the reaction may generally be carried out at a temperature ranging 50° to 150° C. The reaction time is usually in the range of 2 to 30 hours.

(3) The thiazolidine derivative (I) can also be produced by reacting compound of the formula:

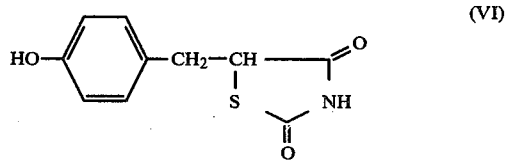

(VI)

with a compound of the formula:

(wherein $L^1$, $L^2$, $R^1$ and $R^2$ have the meanings given above, and $X^2$ means a halogen atom such as chlorine, bromine, etc.) in the presence of a base. As the base, there may be mentioned sodium hydride, potassium carbonate, sodium carbonate, potassium hydroxide, sodium hydroxide, etc. This reaction is usually carried out in the presence of a solvent. As a suitable solvent, there may be mentioned dimethylformamide, dimethylsulfoxide, etc. The reaction temperature may be in the range of room temperature to 100° C.

The resulting thiazolidine derivative (I) can be isolated and purified by conventional procedures such as concentration at atmospheric or subatmospheric pressure, solvent extraction, crystallization, recrystallization, phasic transfer, chromatography, etc.

The compound (III) which is used as the starting material in the above preparation method (1) can be produced, for example, by the steps of diazotizing the corresponding aniline compound and subjecting the diazo-compound to Meerwein arylation.

The following reference and working examples are given to illustrate this invention in further detail.

REFERENCE EXAMPLE 1

In 200 ml of methanol is dissolved 19.0 g of 4-[2-(N,N-dibutylamino)ethyloxy]nitrobenzene and after 3 g of 10% Pd-C (50% wet) is added, catalytic reduction is carried out at atmospheric temperature and pressure. The reaction system absorbs about 4.4 l of hydrogen in 75 minutes. The catalyst is then filtered off, the filtrate is concentrated under reduced pressure and the oily residue is dissolved in a mixture of 100 ml methanol and 100 ml acetone. Following the addition of 21.5 ml of concentrated hydrochloric acid, the solution is cooled to 0° C. and a solution of 4.9 g sodium nitrite in 10 ml water is added dropwise at a temperature not exceeding 5° C. The mixture is stirred at 5° C. for 20 minutes, at the end of which time 33.3 g (34.9 ml) of methyl acrylate is added. The reaction mixture is heated to 35° C. and 1 g of cuprous oxide is added in small portions, whereupon the temperature of the reaction system rises to 44° C. with the evolution of nitrogen gas. The mixture is stirred for one hour and after the temperature has dropped to room temperature, it is allowed to stand overnight. The solvent is then distilled off under reduced pressure and the residue is made strongly basic with concentrated aqueous ammonia. Then, following the addition of water, extraction is carried out with ethyl acetate. The extract is washed with water, dried over sodium sulfate and distilled to remove the ethyl acetate. The oily residue is chromatographed on a column of 200 g silica gel, elution being carried out with ether-n-hexane (1:4). By the above procedure is obtained 10.7 g (44.8%) of methyl 2-chloro-3-{4-[2-(N,N-dibutylamino)ethyloxy]phenyl}propionate.

IR(liquid film) $v_{max}{}^{cm-1}$: 2945, 2850, 1745, 1605, 1505, 1250, 1170, 1030

NMR δppm CDCl$_3$: 0.93(6H, t), 1.2–1.8(8H,m), 2.52(4H,t), 2.83(2H,t), 3.0–3.5(2H,m), 3.7(3H,s), 4.0(2H,t), 4.4(1H,t), 6.75–7.30(4H,q)

EXAMPLE 1

(a) A mixture of 3.6 g of ethyl 2-chloro-3-[4-(2-methyl-2-phenylpropyloxy)phenyl]propionate, 0.73 g of thiourea and 3 ml of sulfolane is heated at 120° C. for 4 hours and after cooling, 15 ml of water is added. The oil is separated, ether is added to the oil and the crystalline insolubles (a) are separated from the solution (b) by filtration. The filtrate (b) is distilled to remove the solvent and the residue is run onto a column of 100 g silica gel, elution being carried out with chloroform. By the above procedure is obtained 1.7 g of 5-[4-(2-methyl-2-phenylpropyloxy)benzyl]thiazolidine-2,4-dione. m.p. 107°–108° C. (benzene-ligroin)

On the other hand, crystals (a) are recrystallized from ethanol-acetone (3:1) to obtain 1 g of 2-imino-5-[4-(2-methyl-2-phenylpropyloxy)benzyl]thiazolidin-4-one with a decomposition point of 210°–212° C. A 300 mg portion of this crystalline product is boiled with 2 ml of sulfolane and 2 ml of 6 N-HCl at 110° C. for 5 hours. After cooling, 50 ml of water is added and the resulting crystals are recrystallized from benzene-ligroin. By the above procedure is obtained 250 mg of 5-[4-(2-methyl-2-phenylpropyloxy)benzyl]thiazolidine-2,4-dione.

EXAMPLE 2

A mixture of 27 g of ethyl 2-chloro-3-[4-(2-methyl-2-phenylpropyloxy)phenyl]propionate, 11 g of thiourea and 60 ml of sulfolane is heated at 110° C. for 6 hours and, then, boiled with 10 ml of 2 N-sulfuric acid (or 2 ml of 6 N-HCl) for 16 hours. After cooling, 1 l of water is added and the oil is separated and allowed to stand for a while, whereupon crystals separate out. These crystals are recrystallized from benzene-ligroin. By the above procedure is obtained 19.9 g of 5-[4-(2-methyl-2-phenylpropyloxy)benzyl]thiazolidine-2,4-dione.

EXAMPLE 3

(a) 333 mg of 2-chloro-3-[4-(2-methyl-2-phenylpropyloxy)phenyl]propionic acid and 150 mg of thiourea are heated with 2 ml of sulfolane at 120° C. for 1.5 hours and, following the addition of 2 ml of 6 N-HCl, the mixture is further heated for 5 hours, at the end of which time 10 ml of water is added. The resulting crystals are recovered by filtration. By the above procedure is obtained 310 mg of 5-[4-(2-methyl-2-phenylpropyloxy)benzyl]thiazolidine-2,4-dione.

(b) The same procedure as that described in (a) is repeated except that 355 mg of sodium 2-chloro-3-[4-(2-methyl-2-phenylpropyloxy)phenyl]propionate is employed. By this procedure is obtained 310 mg of 5-[4-(2-methyl-2-phenylpropyloxy)benzyl]thiazolidine-2,4-dione.

(c) The same procedure as that described in (a) is repeated except that 332 mg of 2-chloro-3-[4-(2-methyl-2-phenylpropyloxy)phenyl]propionamide is employed. By this procedure is obtained 340 mg of 5-[4-(2-methyl-2-phenylpropyloxy)benzyl]thiazolidine-2,4-dione.

(d) In 10 ml of ethanol are dissolved 1.8 g of ammonium 2-chloro-3-[4-(2-methyl-2-phenylpropyloxy)phenyl]propionate and 0.8 g of thiourea and the solution is heated for 5 hours, at the end of which time 50 ml of water is added.

By the above procedure is obtained 1.6 g of 2-imino-5-[4-(2-methyl-2-phenylpropyloxy)benzyl]thiazolidin-4-one.

EXAMPLE 4

In 2 ml of dimethylsulfoxide are dissolved 200 mg of 2-bromo-3-[4-(4-chlorobenzyloxy)phenyl]propionic acid and 100 mg of thiourea and the solution is heated at 110° C. for 3 hours. Then, after 0.5 ml of water is added, the solution is further heated for 5 hours. Then, 10 ml of water is added and the resulting crystals are recovered by filtration and recrystallized from benzene-n-hexane (1:1). By the above procedure is obtained 170 mg of 5-[4-(4-chlorobenzyloxy)benzyl]thiazolidine-2,4-dione.

EXAMPLE 5

1.9 g Of ethyl 3-[4-(2-methyl-2-phenylpropyloxy)phenyl]-2-thiocyanatopropionate is dissolved in 20 ml of ethanol and to the solution 20 ml of 6 N-hydrochloric acid is added. The mixture is refluxed for 24 hours. After cooling, water is added to the mixture. The mixture is subjected to extraction with ether. The extract is washed with water and then dried. After distilling off ether, the residure is crystallized from ether-n-hexane, whereby 730 mg of 5-[4-(2-methyl-2-phenylpropyloxy)benzyl]thiazolidine-2,4-dione is obtained.

EXAMPLE 6

2.1 g Of ethyl 2-methanesulfonyloxy-3-[4-(2-methyl-2-phenylpropyloxy)phenyl]propionate and 0.76 g of thiourea are added to 20 ml of sulfolane, and the mixture is heated at 120° C. with stirring for one hour. After adding 10 ml of 2 N-hydrochloric acid, the mixture is heated at 100° C. for 8 hours. After cooling, water is added to the mixture, and the mixture is subjected to extraction with ether. The extract is washed with water and dried. The ether is distilled off to give 1.3 g of 5-[4-(2-methyl-2-phenylpropyloxy)benzyl]thiazolidine-2,4-dione.

EXAMPLE 7

2.0 g Of ethyl 2-methanesulfonyloxy-3-[4-(1-methylcyclohexylmethyloxy)phenyl]propionate and 760 mg. of thiourea are added to 20 ml of ethanol. The mixture is refluxed for 2 hours. To the mixture is added 10 ml of hydrochloric acid, and the mixture is further refluxed for 16 hours. After cooling, water is added to the mixture. The mixture is subjected to extraction with ethyl acetate. The extract is washed with water and dried. The ethyl acetate is distilled off to give 1.4 g of 5-[4-(1-methylcyclohexylmethyloxy)benzyl]thiazolidine-2,4-dione. Crystallization from 85% ethanol gives crystals melting at 130°–131° C.

EXAMPLE 8

To 12 ml of dimethylsulfoxide is dissolved 1.12 g of 5-(4-hydroxybenzyl)thiazolidine-2,4-dione, and 480 mg of 50% sodium hydride in oil is added to the solution. The mixture is stirred at room temperature for 15 minutes, to which is added 0.81 g of 4-chlorobenzyl chloride. The whole mixture is stirred at 50° C. for 4 hours. Water is added to the mixture and the mixture is acidified with 2 N-hydrochloric acid. The mixture is subjected to extraction with ether. The extract is washed with water and dried. Ether is distilled off to give an oily substance. The oily substance is subjected to column chromatography on 30 g silica gel, elution being carried out with cyclohexane-ethyl acetate (2:1). By the above procedure there was obtained 425 mg of 5-[4-(4-chlorobenzyloxy)benzyl]thiazolidine-2,4-dione.

EXAMPLE 9

By procedures analogous to those described above in Examples 1 to 4, the following compounds were synthesized.

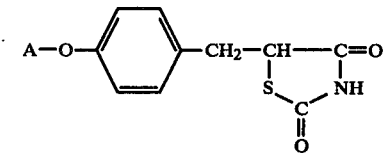

| Compound No. | A | Recrystallization solvent | m.p. (°C.) | Analogous Example No(s). |
| --- | --- | --- | --- | --- |
| 1 | 2-Cl-C₆H₄-CH₂— | Benzene-n-hexane | 85–86 | 1,4 |
| 2 | 4-Cl-C₆H₄-CH₂— | Benzene-cyclohexane | 135–136 | 1 |
| 3 | (CH₃)₃C-CH₂— | Benzene-ligroin | 156–158 | 1,3 |
| 4 | C₂H₅-C(CH₃)₂-CH₂— | Isopropyl ether | 128–129 | 1 |

-continued

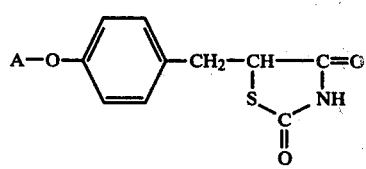

| Compound No. | A | Recrystallization solvent | m.p. (°C.) | Analogous Example No(s). |
|---|---|---|---|---|
| 5 | n-C$_3$H$_7$-C(CH$_3$)(CH$_3$)-CH$_2$- | Ether-n-hexane | 103-104 | 1,2 |
| 6 | n-C$_4$H$_9$-C(CH$_3$)(CH$_3$)-CH$_2$- | Cyclohexane | 102-103 | 1 |
| 7 | n-C$_5$H$_{11}$-C(CH$_3$)(CH$_3$)-CH$_2$- | Cyclohexane | 101-102 | 2 |
| 8 | n-C$_6$H$_{13}$-C(CH$_3$)(CH$_3$)-CH$_2$- | Cyclohexane | 101-102 | 2 |
| 9 | n-C$_7$H$_{15}$-C(CH$_3$)(CH$_3$)-CH$_2$- | Cyclohexane | 101-102 | 2 |
| 10 | CH$_3$-C(CH$_3$)(CH$_3$)-CH$_2$CH$_2$- | Ether-n-hexane | 101-102 | 1,2 |
| 11 | n-C$_3$H$_7$-C(C$_2$H$_5$)(C$_2$H$_5$)-CH$_2$- | n-Hexane | 69-70 | 2 |
| 12 | C$_6$H$_5$-CH$_2$-CH$_2$- | Benzene-ligroin | 93-94 | 1,3 |
| 13 | C$_6$H$_5$-CH$_2$CH$_2$CH$_2$- | Ethyl acetate-cyclohexane | 79-80 | 1 |
| 14 | C$_6$H$_5$-CH$_2$CH$_2$CH$_2$CH$_2$- | Ethyl-acetate-cyclohexane | 82-83 | 1 |
| 15 | CH$_3$-C$_6$H$_4$-CH$_2$CH$_2$- | Ethyl acetate-n-hexane | 130-131 | 2 |
| 16 | C$_2$H$_5$-C$_6$H$_4$-CH$_2$CH$_2$- | Ether-n-hexane | 97-98 | 2 |

-continued

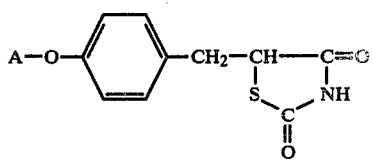

| Compound No. | A | Recrystallization solvent | m.p. (°C.) | Analogous Example No(s). |
|---|---|---|---|---|
| 17 | 4-Cl-C6H4-CH2CH2- | Ethyl acetate | 148–149 | 2 |
| 18 | 4-CH3O-C6H4-CH2CH2- | Ethyl acetate-n-hexane | 104–105 | 2 |
| 19 | 2-OCH3-C6H4-CH2CH2- | Ether-n-hexane | 72–73 | 2 |
| 20 | 4-C2H5O-C6H4-CH2CH2- | Ethyl acetate-n-hexane | 102–103 | 2 |
| 21 | 3,4-(CH3O)2-C6H3-CH2CH2- | Ether-n-hexane | 110–111 | 2 |
| 22 | 3,4-(C2H5O)2-C6H3-CH2CH2- | Oil IR(cm$^{-1}$) 3200, 1750, 1700, 1240 liquid film | | 2 |
| 23 | 2-OCH3-4-CH3-C6H3-CH2CH2- | Ethyl acetate-n-hexane | 92–93 | 2 |
| 24 | 3,4,5-(CH3O)3-C6H2-CH2CH2- | Ethyl acetate-n-hexane | 108.5–109.5 | 2 |
| 25 | 3,4-(OCH2O)-C6H3-CH2CH2- | Ethyl acetate-ether | 132–133 | 2 |
| 26 | C6H5-CH2CH(CH3)- | Ether-n-hexane | 84–85 | 1 |

-continued

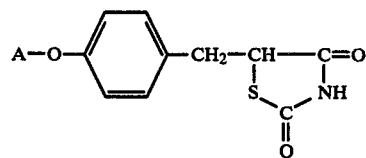

| Compound No. | A | Recrystallization solvent | m.p. (°C.) | Analogous Example No(s). |
|---|---|---|---|---|
| 27 | (phenyl)CH(CH₃)—CH₂— | Ether-n-hexane | 66–67 | 1,3 |
| 28 | (phenyl)CH₂C(CH₃)₂—CH₂— | Ether-n-hexane | 107–108 | 1 |
| 29 | CH₃—(phenyl)—C(CH₃)₂—CH₂— | Cyclohexane | 106–107 | 2 |
| 30 | C₂H₅—(phenyl)—C(CH₃)₂—CH₂— | Ether-n-hexane | 104–105 | 2 |
| 31 | CH₃O—(phenyl)—C(CH₃)₂—CH₂— | Ether-n-hexane | 107–108 | 2 |
| 32 | (3-OCH₃-phenyl)—C(CH₃)₂—CH₂— | Ether-n-hexane | 68–69 | 2 |
| 33 | (2-OCH₃-phenyl)—C(CH₃)₂—CH₂— | Ether-n-hexane | 116–117 | 2 |
| 34 | C₂H₅O—(phenyl)—C(CH₃)₂—CH₂— | Ether-n-hexane | 87–88 | 2 |
| 35 | HO—(phenyl)—C(CH₃)₂—CH₂— | Ether | 157–158 | 2 |
| 36 | 3,4-(CH₃O)₂—(phenyl)—C(CH₃)₂—CH₂— | Ether-n-hexane | 106–107 | 2 |
| 37 | (3-pyridyl)—CH₂— | Methanol | 183–184 | 1 |

-continued

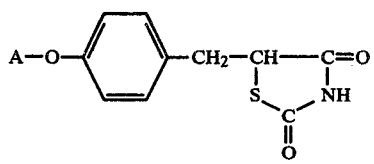

| Compound No. | A | Recrystallization solvent | m.p. (°C.) | Analogous Example No(s). |
|---|---|---|---|---|
| 38 | 3-pyridyl-CH₂CH₂— | Chloroform-methanol | 175–176 | 1,2 |
| 39 | 3-pyridyl-CH₂CH₂CH₂— | Chloroform-methanol | 176–177 | 2 |
| 40 | 2-pyridyl-CH₂CH₂— | DMF—H₂O | 209–210 | 1,2 |
| 41 | 4-pyridyl-CH₂CH₂— | Methanol | 167–168 | 2 |
| 42 | 6-methyl-2-pyridyl-CH₂CH₂— | Ethyl acetate-n-hexane | 103–104 | 2 |
| 43 | 2-thienyl-CH₂CH₂— | Ether-n-hexane | 73–74 | 2 |
| 44 | 2-furyl-CH₂CH₂— | Ether-n-hexane | 62–64 | 2 |
| 45 | 4-methyl-5-(2-)thiazolyl-CH₂CH₂— | Ethanol | 193–194.5 | 1 |
| 46 | cyclohexyl-CH₂CH₂— | Cyclohexane | 82–83 | 1 |
| 47 | cyclohexyl-CH₂— | n-Propanol | 121–122 | 1,2 |
| 48 | 1-methylcyclopentyl-CH₂— | Benzene-ligroin | 137–138 | 1,2 |

-continued

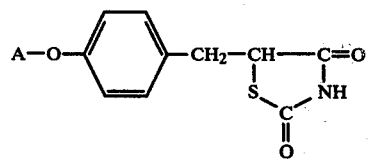

| Compound No. | A | Recrystallization solvent | m.p. (°C.) | Analogous Example No(s). |
|---|---|---|---|---|
| 49 | cyclohexyl-C(CH₂—)(CH₃) | Cyclohexane | 124–125 | 1,5 |
| 50 | cyclohexyl-C(CH₂—)(CH₂CH₃) | Ligroin | 88–89 | 1 |
| 51 | cyclohexyl-C(CH₂—)(CH₂CH₂CH₃) | n-Hexane | 68–69 | 1 |
| 52 | cyclopentyl-C(CH₂—)(phenyl) | Benzene-ligroin | 136–137 | 1 |
| 53 | cyclopropyl-CH₂— | Ether-n-hexane | 88–89 | 2 |
| 54 | cyclopentyl-CH₂— | Ether-n-hexane | 110–111 | 2 |

EXAMPLE 10

A mixture of 10.0 g methyl 2-chloro-3-[4-(2-morpholinoethyloxy)phenyl]propionate and 4.64 g thiourea is heated in the presence of 100 ml of sulfolane at 120° C. for 4 hours. After cooling, a saturated aqueous solution of sodium hydrogen carbonate is added and the mixture is extracted with ethyl acetate. The extract is washed with water, dried over sodium sulfate and distilled to remove the ethyl acetate, whereupon 4.1 g (40.2%) of 2-imino-5-[4-(2-morpholinoethyloxy)benzyl]thiazolidin-4-one is obtained as crystals. These crystals are recrystallized from ethyl acetate-methanol. Colorless needles, m.p. 189°–190° C.

In 50 ml of 2 N-HCl is dissolved 4.1 g of the above 2-imino-5-[4-(2-morpholinoethyloxy)benzyl]thiazolidin-4-one and the solution is heated under reflux for 16 hours. After cooling, the reaction mixture is neutralized with a saturated aqueous solution of sodium hydrogen carbonate and extracted with ethyl acetate. The extract is washed with water, dried over sodium sulfate and distilled to remove the ethyl acetate, whereupon 3.8 g (92.7%) of 5-[4-(2-morpholinoethyloxy)benzyl]thiazolidine-2,4-dione is obtained as crystals. These crystals are recrystallized from dimethylformamide-water. Colorless prisms, m.p. 188°–189° C.

EXAMPLE 11

A mixture of 9.0 g methyl 2-chloro-3-{4-[2-(N,N-diisopropylamino)ethyloxy]phenyl}propionate and 2.4 g thiourea is heated in the presence of 100 ml of n-butanol at 100° C. for 15 hours. After cooling, the n-butanol is distilled off under reduced pressure, 100 ml of 2 N-HCl is added to the residue and the mixture is heated at 100° C. for 6 hours. After cooling, the reaction mixture is neutralized with a saturated aqueous solution of sodium hydrogen carbonate and extracted with ethyl acetate. The extract is washed with water, dried (over Na₂SO₄) and distilled to remove the ethyl acetate, whereupon 6.0 g (65.2%) of 5-{4-[2-(N,N-diisopropylamino)ethyloxy]benzyl}thiazolidine-2,4-dione is obtained as crystals. These crystals are recrystallized from ethanol. Colorless prisms, m.p. 134°–135° C.

EXAMPLE 12

By procedures analogous to those described in Example 10 or 11, the following compounds were synthesized.

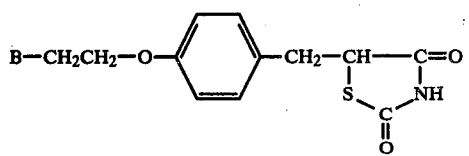

| Compound No. | B | Recrystal- lization solvent | m.p. (°C.) | Analogous Example No(s). |
|---|---|---|---|---|
| 1 | CH₃\N— / CH₃ .HCl | Ethanol | 208–209 | 10,11 |
| 2 | C₂H₅\N— / C₂H₅ .HCl | Ethanol | 146–147 | 10,11 |
| 3 | n-C₃H₇\N— / n-C₃H₇ | Ethanol | 124–125 | 11 |
| 4 | i-C₃H₇\N— / i-C₃H₇ | Ethanol | 134–135 | 11 |
| 5 | n-C₄H₉\N— / n-C₄H₉ | Ethanol | 98–99 | 10,11 |
| 6 | piperidinyl-N— .HCl | Methanol | 232–234 | 11 |
| 7 | piperidinyl-N— .HCl | Methanol | 244–245 | 11 |

EXAMPLE 13

An example of practical recipe in which the compound of this invention is utilized as remedies for diabetes is as follows:

| (Tablet) | | |
|---|---|---|
| (1) | 5-[4-(1-methylcyclohexyl- methyloxy)benzyl] thiazolidine-2,4-dione | 10 mg |
| (2) | lactose | 35 mg |
| (3) | corn starch | 170 mg |
| (4) | microcrystalline cellulose | 30 mg |
| (5) | magnesium stearate | 5 mg |
| | | 250 mg per tablet |

(1), (2), (3) and ⅔ quantity of (4) are thoroughly mixed, and then the mixture is granulated. Remaining ⅓ quantity of (4), and (5) are added to the granules and compressed into tablets. Thus prepared tablets can further be coated with a suitable coating agent.

What is claimed is:

1. A thiazolidine derivative of the formula:

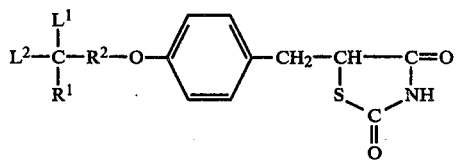

wherein $R^1$ is a pyridyl group having 1 to 3 substituents selected from the group consisting of lower alkyls, halogens and hydroxyl on the ring, or a thiazolyl group having 1 to 3 substituents selected from the group consisting of lower alkyls, halogens and hydroxyl on the ring; $R^2$ means a bond or a lower alkylene group; $L^1$ and $L^2$ are the same or different and each is hydrogen, lower alkyl or $L^1$ and $L^2$ are combined to form an alkylene group.

2. A thiazolidine derivative as claimed in claim 1, each of $L^1$ and $L^2$ is hydrogen.

3. A thiazolidine derivative as claimed in claim 1, wherein $R^2$ is a lower alkylene group having 1 to 3 carbon atoms.

4. A compound as claimed in claim 1, wherein the compound is 5-{4-[2-(6-methyl-2-pyridyl)ethoxy]benzyl}thiazolidine-2,4-dione.

5. A compound as claimed in claim 1, wherein the compound is 5-{4-[2-(4-methyl-5-thiazolyl)ethoxy]benzyl}thiazolidine-2,4-dione.

6. A hypolipidemic and hypoglycemic pharmaceutical composition, which comprises, as an active ingredient, an effective amount of a thiazolidine derivative defined in claim 1 and a pharmaceutically acceptable carrier therefor.

* * * * *